United States Patent
Mansi et al.

(10) Patent No.: US 10,636,142 B2
(45) Date of Patent: Apr. 28, 2020

(54) REAL-TIME AND ACCURATE SOFT TISSUE DEFORMATION PREDICTION

(71) Applicant: Siemens Healthcare GmbH, Erlangen (DE)

(72) Inventors: Tommaso Mansi, Plainsboro, NJ (US); Felix Meister, Erlangen (DE); Tiziano Passerini, Plainsboro, NJ (US); Viorel Mihalef, North Brunswick, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 175 days.

(21) Appl. No.: 15/958,019

(22) Filed: Apr. 20, 2018

(65) Prior Publication Data

US 2019/0325572 A1 Oct. 24, 2019

(51) Int. Cl.
| | |
|---|---|
| *A61B 5/107* | (2006.01) |
| *G06T 17/10* | (2006.01) |
| *G06T 7/00* | (2017.01) |
| *A61B 5/00* | (2006.01) |

(52) U.S. Cl.
CPC .......... *G06T 7/0012* (2013.01); *A61B 5/1075* (2013.01); *A61B 5/1079* (2013.01); *A61B 5/7267* (2013.01); *G06T 17/10* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | |
|---|---|---|---|
| 2003/0118222 A1* | 6/2003 | Foran | G06F 19/321 382/128 |
| 2004/0085443 A1* | 5/2004 | Kallioniemi | G01N 1/36 348/135 |

OTHER PUBLICATIONS

An, Steven S., Theodore Kim, and Doug L. James. "Optimizing cubature for efficient integration of subspace deformations." ACM transactions on graphics (TOG) 27.5 (2008): 165.
Barbič, Jernej, and Doug L. James. "Real-time subspace integration for St. Venant-Kirchhoff deformable models." ACM transactions on graphics (TOG) 24.3 (2005): 982-990
Hauser, Kris K., Chen Shen, and James F. O'Brien. "Interactive Deformation Using Modal Analysis with Constraints." Graphics Interface. vol. 3. 2003.
Hildebrandt, Klaus, et al. "Interactive surface modeling using modal analysis." ACM Transactions on Graphics (TOG) 30.5 (2011): 119.
(Continued)

*Primary Examiner* — Idowu O Osifade (57) ABSTRACT

For soft tissue deformation prediction, a biomechanical or other tissue-related physics model is used to find an instantaneous state of the soft tissue. A machine-learned artificial neural network is applied to predict the position of volumetric elements (e.g., mesh node) from the instantaneous state. Since the machine-learned artificial neural network may predict quickly (e.g., in a second or less), the soft tissue position at different times or a further time given the instantaneous state is provided in real-time without the minutes of physics model computation. For example, a real-time, biomechanical solver is provided, allowing interaction with the soft tissue model, while still getting accurate results. The accuracy allows for generating images of a soft tissue with greater accuracy and/or the benefit of user interaction in real-time.

20 Claims, 4 Drawing Sheets

(56) References Cited

OTHER PUBLICATIONS

Huang, Qi-Xing, et al. "Shape decomposition using modal analysis." Computer Graphics Forum. vol. 28. No. 2. Blackwell Publishing Ltd, 2009.
James, Doug L., and Dinesh K. Pai. "Real time simulation of multizone elastokinematic models." Robotics and Automation, 2002. Proceedings. ICRA'02. IEEE International Conference on. vol. 1. IEEE, 2002.
Jeong, SoHyeon, et al. "Data-driven fluid simulations using regression forests." ACM Transactions on Graphics (TOG) 34.6 (2015): 199.
Kim, Theodore, and Doug L. James. "Skipping steps in deformable simulation with online model reduction." ACM transactions on graphics (TPG). vol. 28. No. 5. ACM, 2009.
McLeod, Kristin, et al. "Atlas-based reduced models of blood flows for fast patient-specific simulations." International Workshop on Statistical Atlases and Computational Models of the Heart. Springer, Berlin, Heidelberg, 2010.
Taylor, Zeike A., Stuart Crozier, and Sébastien Ourselin. "A reduced order explicit dynamic finite element algorithm for surgical simulation." IEEE transactions on medical imaging 30.9 (2011): 1713-1721.
Treuille, Adrien, Andrew Lewis, and Zoran Popović. "Model reduction for real-time fluids." ACM Transactions on Graphics (TOG). vol. 25. No. 3. ACM, 2006.
Wicke, Martin, Matt Stanton, and Adrien Treuille. "Modular bases for fluid dynamics." ACM Transactions on Graphics (TOG). vol. 28. No. 3. ACM, 2009.

\* cited by examiner

REAL-TIME AND ACCURATE SOFT TISSUE DEFORMATION PREDICTION

BACKGROUND

The present embodiments relate to computing soft tissue deformations, such as for medical imaging, computer animation, or gaming. Determining organ deformation may be important for medical image reconstruction, medical image registration, digital twin modeling for data integration and outcome prediction, three-dimensional (3D) mesh editing, augmented or virtual reality, or other applications.

Biomechanical models of soft tissue (e.g., as priors or constraints) may provide more realistic capabilities for determining their deformation under various conditions (e.g. subject to external forces like pressure or gravity, internal forces like stiffness or active stress, etc.). Current state of the art explicitly solves biomechanical equations using the finite element method or other integration methods, given boundary conditions, external forces, constitutive laws and model parameters. Although accurate, these methods are unfortunately time consuming, requiring minutes to hours of computation for a high-fidelity simulation. Real-time solutions exist (e.g., mass-spring or mesh-free models), however at a price for accuracy.

Methods based on machine learning or statistical learning for biophysical simulations have been explored, mostly for computational fluid dynamics (CFD). A common approach (e.g., Proper Orthogonal Decomposition (POD)) estimates a subspace of solutions from a database of simulations. The solutions of the CFD equations are solved in the subspace, and the final solution is reconstructed accordingly. This approach assumes that the solution can be reconstructed by a linear combination of basis functions, which may not be the case. As a result, the accuracy of the reconstructed result could be sub-optimal. Similar approaches have been investigated for soft-tissue mechanics as well and other physical systems.

More sophisticated data-driven techniques have been proposed, such as a random-forest approach to solve in real-time CFD for fluid simulations, based on particle-based solvers. An acceleration at large time step is predicted given the intrinsic properties of a fluid particle and its direct neighborhood. The prediction is a regression model, represented using random forests and trained on thousands of simulations. This approach showed fast simulation performance. However, it is especially tailored to the CFD problem and would not apply directly to biomechanics or other modeling of soft tissue: the states are different, soft tissue are solid material with varying stiffness, and solver stability is much more crucial and difficult to maintain in biomechanics due to the increase stiffness of the partial differential equations. In particular, the random forest approach suffers from high frequency numerical errors that would make the computation not tractable.

Model reduction for fast computation of deformable material has been used with good results in computer graphics, in fluid simulation, in the video game industry and computer assisted design. While these methods perform model reduction on the space of deformations of the object, newer approaches perform reduction on the material model of the object. The range of uses of these methods has not tackled more physiologically accurate, and hence more realistic biomechanical models.

SUMMARY

By way of introduction, the preferred embodiments described below include methods, systems, instructions, and computer readable media for soft-tissue deformation prediction, which combines an finite element solver and artificial neural networks. The proposed embodiments below are described for a biomechanical system, but can also be applied without lack of generality to other biophysiological mechanisms (e.g. electrophysiology, heat conductivity, etc.). The finite element solver of tissue biomechanics (or other type of solvers or tissue-related physics) is used to estimate a representation of the instantaneous state of the tissue at a given point in time. A machine-learned artificial neural network is applied to predict the next position of each volumetric elements (e.g., mesh node) from the instantaneous state. The machine-learned network may predict the soft tissue position at a time farther away than a solver would be able to compute, which are limited by the Courant-Friedrichs-Lewy condition, hence yielding faster computations while being as accurate as numerical solutions calculated using a small time step. For example, a real-time, biomechanical solver is provided, allowing interaction with the model, while still getting accurate results.

In a first aspect, a method is provided for soft tissue deformation prediction. First, multiple soft tissue deformations are simulated with a biomechanics solver for a plurality of samples over time with first temporal increments (e.g., small time step to ensure accurate numerical solutions). An artificial neural network is then trained to predict tissue deformation (e.g., acceleration, velocity, displacement or combination of those) of a mesh node given a representation of the instantaneous state of the soft tissue (e.g., force, velocity, displacement or combination of those), calculated using the biomechanical solver. The predicted tissue deformation is used to determine the soft tissue deformation at a time with a second temporal increment greater than the first temporal increment by at least an order of magnitude. Numerical stabilization techniques like damping or other methods can be used. An image of the soft tissue is generated based on the soft tissue deformation.

In a second aspect, a method is provided for soft tissue deformation prediction by a medical imaging system. The medical imaging system scans a patient. A mesh for one or more organs is estimated from scan data using image segmentation techniques. The mesh represents the organ at a first time. Given mechanical properties (stiffness, forces, boundary conditions from a biomechanical model, a machine-learned artificial neural network predicts a deformation of the mesh at a second time from a mechanical state indicated by the biomechanical model for the first time. The process is iterated to calculate a dynamic representation of the organ deformation. An image, based on the deformation, of the organ is generated. Thanks to the use of the machine-learned artificial neural network, the second time is not limited by the Courant-Friedrichs-Lewy condition of the biomechanical model, hence yielding faster computation times while being as accurate as state of the art solvers.

In a third aspect, a system is provided for soft tissue deformation prediction. At least one medical imaging system is configured to acquire scan data representing a patient. An image processor is configured to model physics in an organ of the patient from the scan data, and to predict a location of the organ by application of a current state from the model of physics to a machine-trained artificial neural network. A display is configured to display an image based on the soft tissue model location. Due to the use of the machine-learned artificial neural network, the soft tissue model location prediction is for a time not limited by the Courant-Friedrichs-Lewy condition of the biomechanical model, hence yielding faster computation times while being as accurate as state of the art solvers.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Biomechanical or other physics-based solvers are limited in the size of time increment used to solve the associated partial differential equations by the Courant-Friedrichs-Lewy condition. For animation, gaming, and/or medical imaging, this may result in non-real-time modeling, hindering their use in these industries. To overcome this problem, a machine-learned artificial neural network is used to predict the output of the physics-based model at any time step, including increments greater than the Courant-Friedrichs-Lewy condition for the solver. This may allow real-time and/or more rapid tissue deformation computation in animation, gaming, and/or medical imaging. In the examples below, medical imaging is used. The same approaches or embodiments may be applied for tissue deformation in animation, gaming, or other computer-based modeling of soft tissue without loss of generality.

Real-Time determination of soft tissue (bio)-physics uses a learned deep neural network. A deep-learning approach solves the tissue (bio)-physical model, such as any biomechanical, electrophysiology, or heat transfer model. For the case of tissue biomechanics, an artificial neural network is trained to regress a biomechanics characteristic (e.g., but not limited to, force, velocity, acceleration, displacement, or a combination thereof) at large time steps, $D_t$, of each node of a 3D mesh that represent the soft tissue given an instantaneous nodal representation of the biomechanical state of the node. The training uses many (e.g., hundreds, thousands, or millions) of simulation results at small time steps, $d_t$, from the tissue model. The artificial neural network is trained to approximate the underlying tissue model forces or other characteristics while still being parameterized by tissue parameters, and without explicitly learning the very large (infinite) space of possible boundary conditions. In one embodiment, a recurrent neural network is trained to calculate the equivalent total deformation characteristic for the large time step, given the recent history of instantaneous deformation characteristics.

Once trained, the neural network estimates the deformation characteristic at each large time step $D_t$ from the instantaneous nodal deformation characteristics. Where the deformation characteristic is force, velocity, or acceleration, the value of the characteristic is integrated over time to get the new nodal position. The neural network is embedded into the tissue model, such as a Total Lagrangian Explicit Dynamics framework, to estimate the instantaneous deformation characteristics provided as input to the neural network.

Accurate results at large time-steps are provided with efficient computations. Accurate deformation characteristics at very large time steps are estimated, thus yielding high-frame rate (e.g., 10 frames per second (fps), 20 fps, or more) and potentially real-time capabilities. Various medical or other imaging may benefit from the accurate prediction of deformation characteristics, such as imaging for disease understanding, therapy planning, and/or image-guided interventions. Fast, high-fidelity soft tissue deformation is provided by the combination of the physics-based solver with the machine-learned artificial neural network.

Figure 1:
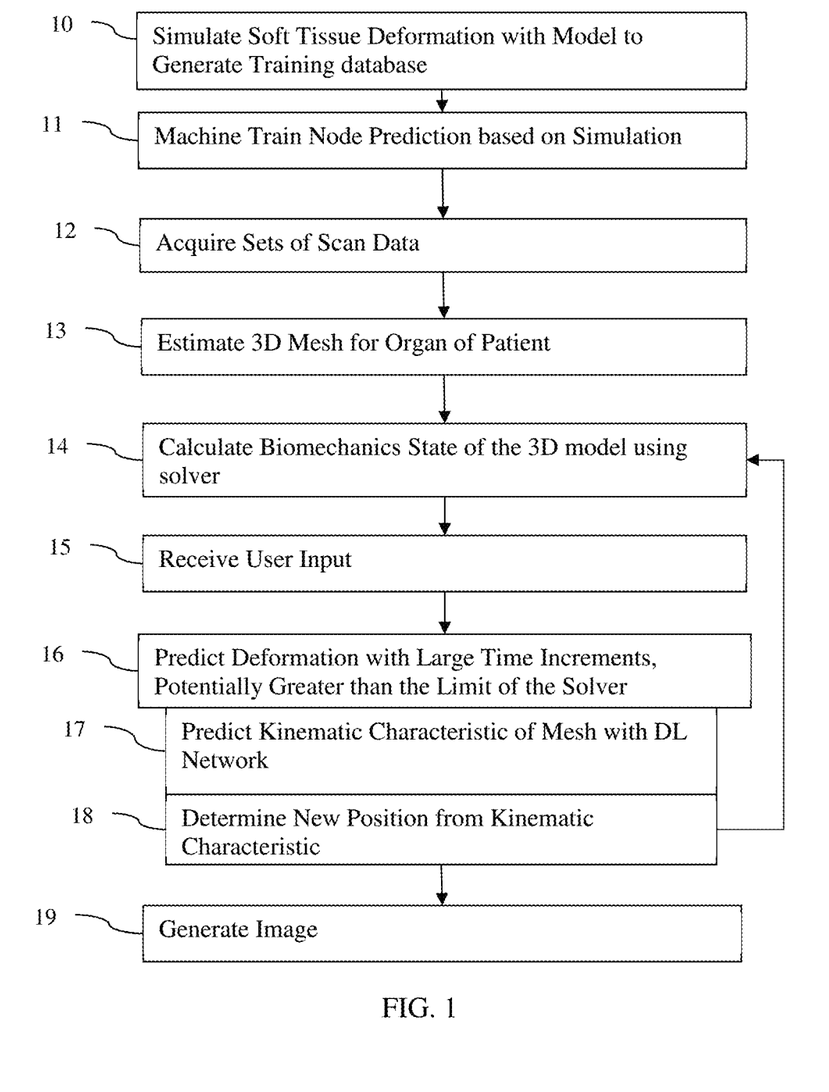
FIG. 1 is a flow chart diagram of one embodiment of a method for organ deformation prediction.

FIG. 1 shows one embodiment of a method for soft tissue deformation prediction by an imaging system, discussed below for medical imaging of a soft tissue. The method simulates tissue deformations by leveraging the universal function approximator capabilities of a neural network. Point-wise deformation characteristics are predicted for a larger time step compared to a finite element solver or other physics-based tissue model. The prediction uses the current or already determined state of the tissue model from the solver. Based on the prediction for the larger time step, the small time step requirement of the explicit solver (e.g., the tissue model) is overcome, cutting down the computational cost to a minimum. A neural network is capable of learning the underlying physics to predict a larger time step.

Figure 4:
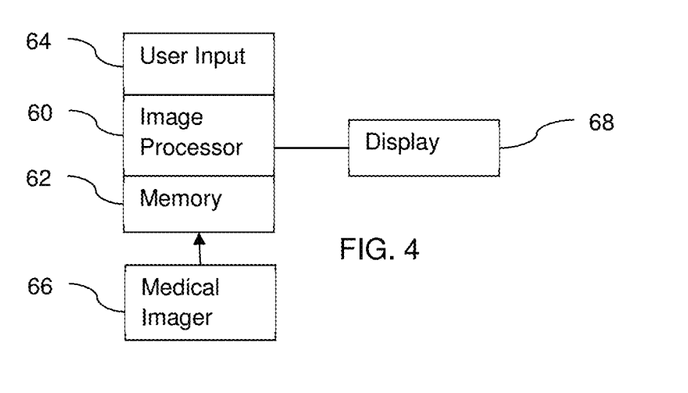
FIG. 4 is one embodiment of a system for organ deformation prediction.

The method is implemented by a medical imaging system, such as the medical imaging system of FIG. 4 or another imaging system. The medical imaging system may be one of various imaging modalities, such as magnetic resonance (MR), computed tomography (CT), ultrasound, nuclear (e.g., PET or SPECT), x-ray, or therapeutic imaging system. In one embodiment, a computer (e.g., workstation or server) simulates and trains. A transmitter and/or receiver scans the patient. For patient specific application of the trained network, an image processor positions a mesh or volume elements, fits a model to the patient-specific mesh, predicts deformation, and generates an output image on a display device. A user input receives user input to interact with the mesh, model, and/or image. The user input, image processor, and/or display device are part of or separate from the imaging modality or scanner.

The acts are performed in the order shown (i.e., top to bottom or numerical order) or other orders. For example, acts 13 and 14 are performed simultaneously or in reverse order. As another example, act 15 occurs after any of acts 12-19.

Additional, different, or fewer acts may be provided. For example, act 15 is not provided. As another example, acts 13 and 14 are combined where fitting the model also positions the mesh. Act 19 may be optional. In another example, acts 10-11 are performed without acts 12-19, or acts 12-19 are performed without acts 10-11. The method includes two phases: training (acts 10-11) and testing (acts 12-19; e.g., patient-specific application of the trained network). In application, acts 16-18 are repeated for different mesh nodes, where acts 14-18 may be repeated for different mesh times to form a sequence.

In act 10, computer creates or loads training data for training with machine learning. For machine training, hundreds, thousands, or millions of samples with ground truth are used. The samples include the ground truth soft tissue deformation (e.g., position of surface locations or volume elements) as well as the data from which the machine learns to predict the ground truth. In one embodiment, the machine learns to predict the acceleration or other deformation characteristic of nodes or other volume elements from a physics model-based state of the soft tissue (e.g., from instantaneous forces for that node or volume element derived from the physics model, the instantaneous velocity and/or relative displacement with respect to the rest/initial position).

In one embodiment, the training data is generated from medical scans. A physician or expert segments medical imaging scan data representing the patient over time. For 3D imaging, creating many samples with ground truth locations is time consuming done manually. In other embodiments, the organ deformation is done as a simulation. The 3D organ mesh or volume element position may be obtained from medical images using machine learning technologies. Any now known or later developed segmentation or organ tracking may be used. By using different patients, the organ deformation for different geometries of the organ is provided. In yet another embodiment, synthetic samples are used. A model of a soft tissue over time provides the deformation information to learn from. The synthetic model may be from a physical model, such as tubes emulating vessels. The synthetic model may be from random or designed perturbation of mesh or soft tissue representation from an atlas or actual patients. Many samples of soft tissue deformation over time may be generated.

The training data is for a specific application. For example, the training data and corresponding machine training is specific to an organ of interest (e.g., liver or vessel), application, physics model, and/or imaging modality.

A physics model of tissue (e.g., tissue model such as a biomechanical solver) known to be accurate generates the samples from the meshes or volume elements. Using scan data from different patients, synthetic data, and/or manually segmentations over time, the tissue model is fit to the patients. The tissue model is fit to the organ. The tissue model provides parameters (e.g., force, velocity, acceleration, and/or position) for different volume elements (e.g., nodes) at different times. For example, a verified biomechanical solver (e.g., finite element method) is used to determine the values of parameters (e.g., forces) at the time increments. Boundary conditions are estimated using images or user interactions.

The simulation models the organ deformation using time increments. Any time increment may be used, such as millisecond time increments. In one example, the time increment for the model is limited to 0.0003 s. The time increment is at the Courant-Friedrichs-Lewy condition or less. In this example, 0.0003 s was the largest time step possible for an explicit solver. The simulation provides soft tissue deformation as a sequence of meshes or volume element position over time at a temporal resolution provided by the time increment. The tissue model operates at the temporal resolution to provide the parameters at the time increments.

A sequence of meshes or volume element positions over time represents the deformable soft tissue. A change in the nodal or element position indicates the soft tissue deformation. This deformation is simulated using the time increments, providing samples over time at the time increments.

For learning to predict organ deformation, the training data includes the information from which the prediction is to be made. For emulating the tissue model, the parameters of the tissue model may be used rather than or in addition to the mesh or volume element position. For example, the position, $x(t)$, of each node of the organ mesh model in 3D is used. In another embodiment, the displacement $u(t)=x(t)-x(0)$ is used. One or more (e.g., all) forces applied to each node, $f_e(t)$ (e.g., gravity, electromagnetic, and/or contact force) are used. One or more (e.g., all) forces applied to external surfaces, $f_s(t)$ (e.g., pressure or contact force), redistributed to each node or volume element following discretization methods, are used. One or more (e.g., all) forces applied to volumetric elements (e.g. tetrahedron), $f_v(t)$ (e.g., internal stiffness and/or active forces (e.g., stress from muscle operation)), redistributed to each node following discretization methods, are used. The biomechanical model, based on being fit to the meshes or scan data, provides the values for the forces or a sum of forces. In other embodiments, values of other parameters of the tissue model or derived from the tissue model are used instead of or in addition to the forces. In other embodiments, the values for the forces are also learned using machine learning. The parameters are 3D (e.g., 3D vectors for force), but 2D, 1D, or non-spatial parameters may be used.

In act 11, the image processor applies machine training. An artificial neural network is machine trained to predict organ deformation, such as acceleration or other deformation characteristic of an organ position, as a function of time from locations and the values of the parameters from the tissue model, such as instantaneous forces of the samples over time with the first temporal increments from the biomechanical solver.

Deep learning is used to train the artificial neural network. Any deep learning approach or architecture may be used. For example, a convolutional neural network is used. The network may include convolutional, sub-sampling (e.g., max pooling), fully connected layers, and/or other types of layers. Any combination of layers may be provided. Hierarchical structures are employed, either for learning features or representation or for classification or regression.

The deep machine-learnt classifier learns filter kernels, connections, weights, or other features that indicate the deformation or may be used to determine deformation. Rather than or in addition to outputting the deformation, features useable to determine the deformation are learned using deep learning. For example, the acceleration by node is to be output. The deep machine learning uses training data, such as information by node, by patch or sub-group of nodes (e.g., neighborhoods), or all the nodes (e.g., mesh). The deep leaning provides a deep machine-learned network that outputs the results.

In one embodiment, the neural network, NN(f), is trained to work with a biomechanical model, such as a total Lagrangian Explicit Dynamics (TLED) algorithm based on a finite element method. The biomechanical model determines a sum of forces at each node of a 3D mesh of the soft tissue. The sum is represented as $f(t)=f_e(t)+f_s(t)+f_v(t)$. The neural network is trained to return the acceleration $a(t)$ to move the node or volume element vertex, $x(t)$, to a deformed position, $x(t+D_t)$, where $D_t$ is a significantly higher time step than $d_t$ used as the time increment in the biomechanical model. $Dt \gg dt$ (at least one or two orders of magnitude, more if possible). For example, the time step for neural network prediction is 500 or more (e.g., 1,000 or more) than the time increment of the simulations for creating the training data.

Any physics-based tissue or biomechanical model may be used. In one embodiment, the biomechanical model is for an organ of soft tissue. The soft tissue deformation involves solving an underlying dynamics equation:

$$M\ddot{u}+D\dot{u}+Ku=f_e \quad (1)$$

where M is the lumped mass matrix, D=uM is the Rayleigh damping, and K is the stiffness matrix. $\ddot{u}$, $\dot{u}$, and u are the vertex acceleration, velocity, and displacement, and $f_e$ are external forces. Hyper-elastic material is assumed, and a simplified version of the Holzapfel-Ogden model is employed, although any other elastic, hyper-elastic, or plastic model may be used. In the case of hyper-elastic tissue model, the stress-strain energy function provides: $\psi=a/(2b) \exp(b(I_1-3))+a_f/(2bf)\{\exp(b_f(I_{4f}-1)^2)-1\}+d(J-1)$. In this equation, a, b, $a_f$, $b_f$, and d are free parameters, $I_1=tr(C)$ and $I_{4f}=f^T Cf$ are invariants of the deformation tensor C, f is the fiber direction, and J is the Jacobian determinant of the deformation. In the case of isotropic material, $a_f=0$. The TLED algorithm is used to integrate equation (1). TLED uses explicit time integration and a total Lagrangian formulation of the dynamics equation for efficient computation. Using the central difference scheme, the integration step for a step size of $\delta t$ provides:

$$u(t+\delta t)=\alpha(\delta t)f_t(t)+\beta(\delta t)u(t)+\gamma(\delta t)u(t-\delta t) \quad (2)$$

where $$\alpha(\delta t) = \frac{2\delta t^2}{m(2+u\delta t)}, \beta(\delta t) = \frac{4}{(2+u\delta t)}, \gamma(\delta t) = \frac{(u\delta t-2)}{(2+u\delta t)},$$

and $f_t(t)$ is the total force at time t.

Other biomechanical models or integration schemes may be used. For other models, parameters other than force can be used. The network is trained to predict from these other parameters. For other models, an acceleration, velocity, and position formulation may not be used. The network is trained to predict one or more of the parameters used.

The artificial neural network is trained to approximate the biomechanical model, such as to approximate the acceleration, velocity, force, or displacement from instantaneous biomechanical forces. The main computational load in equation 2 is the calculation of the vertex-wise force $f_t$ at every time step. To accelerate the computation time, the force $\ddot{u}_t^{\Delta t}$ that would move the vertex (e.g., mesh node or volume element) from a current position x(t) to anther position $x(t+\Delta t)$, where $\Delta t=N\delta t$ is a larger time step than $\delta t$, is used. In another embodiment, the force $f_t$ could be learned directly using another artificial neural network that, given the current position of the soft tissue model, returns the internal stress at each vertex. In a total Lagrangian frame, a biomechanical system is fully characterized at any point in time by its displacement u(t)=x(t)−x(0), velocity $\dot{u}(t)$, and the forces and boundary conditions being applied f(t). Different tissue models may deal with different forces, such as a biomechanical model limited to modeling internal elastic forces, surface pressure, and spatially-constant external forces like gravity. The model is translation and rotation-invariant. The model is characterized using only the velocity and total forces. Let $\phi(t)$ be the state vector of a vertex at time t, $\phi(t)=(\dot{u}(t), f_t(t))$.

For machine training in this arrangement, the regression function R in $\ddot{u}_t^{\Delta t}=(R(\phi(t), \phi(t-\Delta t), \ldots, \phi(t-L\Delta t))$ is learned, where the L last time steps are considered to improve the prediction accuracy, using neural networks. The new position is then calculated using the following numerical scheme with a time step of $\Delta t$.

$$u_{t+\Delta t}=\alpha(\Delta t)mA_t^{\Delta t}+\beta(\Delta t)u_t+\gamma(\Delta t)u_{t-\Delta t} \quad (3)$$

The parameters $\alpha$, $\beta$ and $\gamma$ add a damping factor to cope with numerical stability. The velocity for a larger time step is computed using central differences by:

$$v(t) = \frac{u_{t+\Delta t} - u_{t-\Delta t}}{2\Delta t} \quad (4)$$

Figure 2:
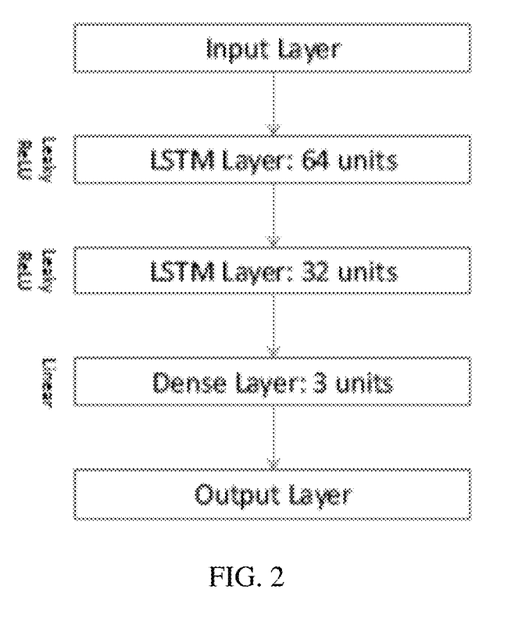
FIG. 2 illustrates an example architecture for an artificial neural network for prediction of soft tissue deformation.

FIG. 2 shows an example artificial neural network architecture to be trained for the regression. The neural network has two parts: sequence feature extraction and acceleration prediction. For the first task, the feature vector from an input layer (e.g., convolutional layer) is passed to stacked long-short-term-memory (LSTM) layers (e.g., sequence of 64 and 32 hidden unit layers) or gated recurrent units. The output is then put through a linear dense layer (e.g., 3 hidden units) to predict the wanted accelerations (e.g., x, y, and z components of acceleration). As an activation function, a leaky rectified linear unit is used on all the layers, except the output dense layer, where a linear function is applied as an activation function. Other network architectures with other activation function could be considered without lack of generality.

The network is trained for any number of epochs (e.g., 15) using any optimization, such as Adam, a learning rate of 0.0001, mean-squared error loss or any other loss function, and zero-mean normalization to have an input and output range of [−1, 1]. Other arrangements, layers, units, activation functions, architectures, learning rates, optimizations, loss, and/or normalization may be used. Other architectures dealing with sequential inputs may be used, such as a perceptron-like feed forward model, convolutional neural network, a long-short term memory, and/or a recurrent neural network architecture.

The acceleration or other deformation characteristic is to be predicted for each node. Velocity, displacement, and/or location may be predicted as well. The prediction indicates the deformation by location, velocity, and/or acceleration. The network is trained to be generic to the nodes, so may be applied as trained to any mesh node. The prediction may be for volumetric elements (e.g., tetrahedron) and redistributed to nodes. The forces or other tissue model parameters and the location for a given node or element is used to predict. In other embodiments, information for neighboring nodes or elements is used for predicting for each node or element.

The neural network is trained to learn the underlying physics to predict point-wise accelerations to move for a larger time step compared to the original finite element solver. The network generalizes well for arbitrary shapes, forces, and various material properties. In one embodiment for liver deformation, only synthetic data is used for training. 400 simulations are created in act 10 using TLED on a time step of 1e-5 seconds. The data is split into 8 different kinds of motion. Hyperlattice cube sampling randomizes the material properties, forces, and frequency of force change in the synthetic data. The ranges are [(1,5), (10,15)], [−0.25, 0.25], and [1 Hz, 4 Hz], respectively, but other ranges may be used. The bulk modulus is set at 1 kPa, but other bulk modulus values may be used. Furthermore, the initial 0.1 seconds of each simulation is removed to remove transient effects in the training dataset, which produces high-frequency noise mostly due to numerical integration. From the remaining frames or times, 1000 frames are randomly subsampled. For each of these frames, all points or nodes are used. The training dataset is split, using 80% for training and 20% for validation. Other settings may be used.

Once trained, the machine-learned artificial neural network predicts acceleration or other representation of deformation (e.g., force, velocity, or displacement). Based on input of instantaneous values of parameters of or from the tissue model and the location of the node or volume element, the machine-learned network outputs the prediction. The trained network is stored for patient-specific application.

For patient-specific application, a medical imaging system scans a patient in act 12. One or more medical imaging scanners or systems acquire sets of scan data. The sets of scan data are acquired by scanning the patient. Alternatively, an image processor acquires the sets of scan data from one or more memories, databases, scanners, and/or via transfer over a computer network. Sets of scan data from previously performed scans are retrieved.

Each set is from a different time and/or modality. For example, one set of scan data is from a previous patient visit, such as weeks, months or years earlier. The same or different scanner scans the patient using the same or different settings at each visit. In another example, different modalities of scanners are used, such as CT or MRI for a preoperative scan and ultrasound or x-ray during an operation. Any type of scan data and corresponding modality of scanner may be used. Any of CT, x-ray, MR, ultrasound, PET, SPECT, fluoroscopy, angiography, or other scanner provides scan data representing a patient.

By using scan data from different times, changes over time may be viewed. The tissue or anatomy represented in one set of scan data may be deformed relative to the tissue or anatomy representing in another set of scan data. For example, a location in one set of scan data may be in the lungs, but that same location in another set may be in a bone. Due to the differences in time of acquisition and/or length of time to acquire, the different sets of scan data may be subject to different motion and corresponding position. Similarly, different imaging systems have different coordinate systems, so may provide different tissue at different locations. Physiological cycles (e.g., heart or breathing) may displace tissue in one set compared to another set. Patient and/or scanner motion may cause relative displacement. The relative displacement is rigid (i.e., the same for the entire frame of scan data) or non-rigid (i.e., affine where some locations are displaced by different amounts and/or directions than other locations). In other embodiments, the scanning repeats and the organ deforms over time due to any of various reasons, such as contact force on the patient, surgical intervention, muscle operation, breathing motion, and/or cardiovascular motion.

The scan data, or medical imaging data, is a frame of data representing the patient. The data may be in any format. While the term "image" is used, the image may be in a format prior to actual display of the image. For example, the medical image may be a plurality of scalar values representing different locations in a Cartesian or polar coordinate format the same as or different than a display format. As another example, the medical image may be a plurality red, green, blue (e.g., RGB) values to be output to a display for generating the image in the display format. The medical image may be currently or previously displayed image in the display format or other format.

The set or frame of scan data or image represents a volume of the patient. The patient volume includes all or parts of the patient. The volume and corresponding scan data represent a three-dimensional region rather than just a point, line or plane. For example, the scan data is reconstructed on a three-dimensional grid in a Cartesian format (e.g., N×M×R grid where N, M, and R are integers greater than one). Voxels or other representation of the volume may be used. The scan data or scalars represent anatomy or biological activity, so is anatomical and/or functional data. Alternatively, the scan data represents a two-dimensional region or plane within the patient.

In act 13, an image processor positions a mesh for an organ. The mesh is for part of an organ, such as a vessel, or the whole of an organ, such as the liver. The mesh is for an outer or interior surface. The mesh represents the organ. In other embodiments, volume elements on the surface and/or within tissue are positioned.

The mesh is estimated from the scan data. The scan data representing the organ at a given time is used. The mesh may be estimated from scan data representing the organ at other times.

For mesh estimation, the tissue as represented by the scan data is segmented. A surface or volumetric fitting may be used. Thresholding or other image processing may be used to identify the surface or parts of the organ. In one embodiment, a machine-learnt classifier or segmentation is applied to detect the locations of the organ. In yet another embodiment, a model of the organ is fit to the scan data, where the fit model provides the mesh. The mesh represents the patient-specific spatial distribution of the patient's organ.

In act 14, the image processor defines the tissue model (i.e., physics-based solver) based on the mesh and/or scan data. For a physics-based tissue model, the fitting solves for various parameters to provide the mesh shape over time. Any tissue model and corresponding fitting may be used. For example, a biomechanical model is fit to a sequence of meshes over time to solve for various forces and/or parameters that result in various forces. In an optimization, different values of parameters of the tissue model are tested. The resulting differences between the tissue model prediction and the scan data and/or positioned mesh or meshes are used as feedback to find the values of the parameters of the tissue model best matching the patient. In one embodiment, solving for the tissue model parameters also provides the mesh.

The fit tissue model is operated for a period, such as modeling the organ and deformation through time increments totaling 1-3 seconds. This modeling may take minutes. The values of various parameters, such as the forces, a sum of forces, tissue characteristics, and/or other parameters are used and/or determined for each time increment. The values for a given time increment represent instantaneous values.

In act 15, a user input receives input from the user. A graphics user interface generated by the image processor or a control processor receives information from the user. The user may view an image of the organ and/or mesh and indicate a change. For example, the user may adjust locations of one or more nodes of the mesh. As another example, the user may indicate a surgical change to be made, resulting in a change in the mesh. In yet another example, the user indicates a path for intervention, which path may apply pressure or force to the organ. In other embodiments, the user changes one or more values of parameters of the model. Constraints may be changed. Rather than changes, the user may enter initial values and/or locations.

One advantage of predicting deformation by combining a machine-learned network with a biomechanical solver is that a forward system is solved. The user may interact with the model, adding boundary conditions and/or forces not directly seen during training. Added force may be any combination of external, surface, or volumetric forces. Rather than waiting for time consuming computation for the tissue model to solve for deformation, the machine-learned network is used to predict the deformation resulting from the changes. Since a large time step may be used in the prediction and application of the trained network by the image processor is more efficient than using just the tissue model, the results may be provided in real-time.

The prediction is based, in part, on the user input. The prediction occurs within a second, such as within microseconds, of receiving the user input. The user inputs a change, and the deformation resulting from that change is predicted quickly or in real-time. The result is provided more quickly by the image processor than if the tissue model were used without the trained network. For example in modeling compression of a bar shape or liver, a timestep limit (CFL limit) of the solver is 0.0003 s. Using the machine-learned neural network, a time step of 0.0006 s is used predict cylinder compression, liver compression and bar stretching at a timestep $dt_{predict}=2*dt_{train}$, i.e. twice as fast). An image showing the results of the change may be generated interactively with the user as the user enters changes.

In act 16, the image processor predicts a deformation of the mesh or volumetric element. The deformation of the organ is predicted as a deformation in the mesh or relative placement of a volumetric element. The position of part of the organ is predicted as a nodal position of the mesh. This change in position or the absolute position provides a deformation. The prediction of the deformation may be a predication of velocity, acceleration, force, displacement, position or other deformation/kinematic characteristic of a node or volumetric element. The prediction may be relative, such as the position of one node relative to another node.

The image processor predicts, at least in part, using the trained neural network. By application of an input feature vector, the machine-learned network outputs the prediction. The prediction is of the deformation or change over time. The predication is of the location or position of the mesh (e.g., node) at a different time. Rather than using the tissue model to solve for the deformation through many time increments to reach a different time (forward or reverse in time), the machine-learned network predicts the deformation of the organ at the other time.

The time increment used for prediction may be greater than the time increment used in simulations for the training data, such as being at least one, two, or more orders of magnitude (e.g., 10×) greater while still being within 10% level of accuracy of the tissue model. In some embodiments, the time increment is at least 500 or 1000 times greater than the time increment used in the simulation with the tissue model. The computation time is reduced by the same magnitude, allowing real-time framerates for estimating deformation. In alternative embodiments, the same time step is used for training and prediction.

The prediction may be repeated for different nodes or volume elements. The same machine-learned network is used to predict deformation for each, all, or a sub-set of the nodes or volume elements. The prediction may be repeated for various times, such as predicting for different times corresponding to a sequence of incremental time steps (e.g., predicting at each time step $D_t$. The node location in 3D space, x(t), for each node at each time step is predicted.

The prediction is based on the input vector. The input vector is values for one or more parameters of the tissue model. For example, a mechanical state indicated by the biomechanical model at an initial or given time is input. The organ position for a patient is predicted from a current location of the node and instantaneous values of parameters of the biomechanical solver fit to the patient. Past or other estimated locations and instantaneous values may be input as well.

In one embodiment, the input of the mechanical state to the machine-learned network is a sum of instantaneous forces and/or values for different instantaneous forces. For example, a sum of external forces, surface forces, and internal forces is input as a 3D vector with the location. The values of tissue characteristics and other parameters from the fit biomechanical model may be used to determine the force or forces in 3D at each node or volume element. As another example, all external forces applied to each node, $f_e(t)$ (e.g. gravity), all forces applied to external surfaces, $f_s(t)$ (e.g., pressure), and/or all forces applied to volumetric elements (e.g. tetrahedron), $f_v(t)$ (e.g., internal stiffness and/or active forces) are input. The forces included in the tissue model are input. One or more of the forces may result from user interaction. Alternatively, none of the forces result from user interact or change. The external forces and/or volumetric forces may be redistributed to each node by discretization, so node specific forces are determined.

In response to the input, the machine-trained network regresses the acceleration, as represented by: $a(t)=NN(f)$, with $f(t)=f_e(t)+f_s(t)+f_v(t)$. The acceleration as the kinematic characteristic is predicted in act 17 by the machine-learned network in response to input of the force or forces and the location from one or more times. The instantaneous values for the forces or other parameters and the instantaneous values for the locations from different times may be input as a time course for prediction. Alternatively, the instantaneous values for one time are input.

In act 18, the image processor predicts the position of the node or volumetric element from the predicted kinematic characteristic (e.g., acceleration) or other predicted parameter. The output of the machine-learned network may be the deformation (e.g., position) or may be a value (e.g., a force or forces, velocity, displacement, and/or acceleration) used to derive the deformation.

In one embodiment, the image processor performs one or more temporal integrations. The nodal location of the mesh is determined from a temporal integration of the acceleration. The temporal integration of acceleration provides a velocity. For example, the image processor integrates over time to get the velocity, as represented by: $v(t+Dt)=a(t)*Dt+v(t)$. The nodal location may be determined from a temporal integration of the velocity. For example, the image processor integrates over time to get the position, as represented by $x(t+Dt)=v(t+Dt)*Dt+x(t)=a(t)*Dt*Dt/2+v(t)*Dt+x(t)$. The time step is the larger time step provided by or used for the application of the machine-learnt network. Any other temporal integration schemes may be used (implicit, explicit), at any order (Euler, Runge Kutta, etc.). The nodal location then indicates, for that part of the mesh, the organ position (e.g., a surface location of the organ).

Boundary conditions may be applied to the acceleration, velocity, and/or nodal location. The boundary conditions may be a range, a constraint, a weight, or any other check. For example, the acceleration is limited to a range of possible values. Any acceleration beyond the range (magnitude and/or direction) is treated as invalid, and the deformation determination ceases.

The predication is repeated for each node or group of nodes. Using the same time increment, the deformation at different organ positions is determined. The surface of the organ or volume elements of the organ are provided at two or more times, showing the deformation.

In act 19, the image processor generates an image. The image is a medical image of the patient for diagnosis, prognosis, and/or treatment. The image is displayed on a display device or screen of a medical scanner. Alternatively, the image is displayed on a workstation, computer, or other device. The image may be stored in and recalled from a PACS memory.

The medical image is generated using or based on the deformation. In one embodiment, the mesh or volume elements as deformed to a particular time are used. The image represents the organ as deformed, such as displaying a rendering of the mesh.

Other medical imaging may use or be based on the deformation or the organ position determined, at least in part, from the machine-learned network. In one embodiment, a medical image is reconstructed from scan data where the reconstruction uses the organ position. For example, CT, PET, SPECT, or other tomographic imaging uses a biomechanical prior as a constraint during image reconstruction, for instance to reduce motion artifacts. The organ position is used to guide the assignment of location to sensed values in the tomography.

In another embodiment, the medical image is generated with a registration from different scans of the patient where the registration is based on the organ position. Motion compensation and/or multi-modality fusion use the organ position (i.e., accurate biomechanical constraints) to ensure biophysically relevant image fusion. The spatial locations representing the same parts in different scans are aligned or registered. Once aligned, information from both scans is fused into a same image. For multi-modality fusion, information from different modalities of medical imaging are combined in a same image. The combination benefits from accurate alignment, which is provided by the organ positions. For motion compensation, the organ position at different times is used to remove motion artifacts so that the same parts of the organ at different times may be compared.

In another embodiment, the medical image is generated to represent interaction of the organ with a device. The device is modeled to provide contact force on the organ. The resulting deformation of the organ is modeled, such as predicting the deformation with the machine-learned network. An image of the organ as deformed and including a representation of the device is generated.

In yet another embodiment, the medical image is generated to simulate a modeled change where the organ position is used to solve a model used to simulate the modeled change. For example, a digital twin is used. The digital twin is a modeled representation of the organ. The tissue model (e.g., biomechanical solver) provides for deformation, enabling interaction with the organ models for "on-the-spot" clinical decision support. An alteration of the organ model may be made, and the deformation that results is estimated. This deformation is applied to the organ model, and the organ model is rendered to an image. In another example, realistic augmented or virtual reality deforms a model overlaid on an image in a realistic fashion according to biophysical laws as estimated by the tissue model. An image from scan data is augmented with information from the deformed model.

In another embodiment, the medical image is a parameterized image. The tissue mechanics or other characteristic derived from rather than being of intensity of return from scanning is calculated. The calculation is based in part on the motion of the organ. The deformation estimation is used to provide the motion, which is then used to calculate the tissue mechanics value by spatial location, such as cardiac strain or liver stiffness. By enabling real-time biomechanical constraints from deformation, more precise quantification of tissue mechanics may be obtained.

The medical image is generated from data distributed in two or three dimensions. For example, a 3D rendering is performed from preoperative or other scan data. Any 3D rendering may be used, such as alpha blending, maximum intensity projection, volume rendering, surface rendering, and/or path tracing. In another example, values along a plane through a volume are extracted. The values are used to form a two-dimensional image representing the plane. Combinations of two-dimensional and 3D imaging may be used, such as a quad display with three images from different planes and a volume rendering shown on a same screen at a same time.

Replacing or adding to the finite element solver or other tissue model based on physics using artificial intelligence (AI) (e.g., machine-learned network) for some of the times represented by the modeling may be tested. The AI pipeline makes correct predictions. The trained neural network is predictive. This approach is generalizable.

In a first experiment, a neural network is machine trained to predict with the same time step as the original biomechanical solver to show that correct predications are made. Another network is machine trained to predict for a time step ten times larger than the time step of the underlying biomechanical solver (e.g., TLED), and the predictions are compared to estimates from the biomechanical solver with the same larger time step and with a smaller time step (e.g., the same time step as in the first experiment). Each of these networks are trained on bar deformations but are evaluated on a cylinder mesh and a liver mesh to prove that the AI is generalizing well on other geometries.

Figure 3A:
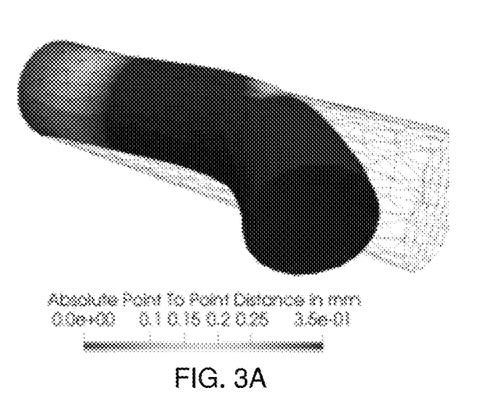
FIGS. 3A-D show example visualization of absolute point-to-point distance between machine-learned artificial neural network-based and a Total Lagrangian Explicit Dynamics (TLED) biomechanical model-based locations for a cylinder and a liver.
Figure 3B:
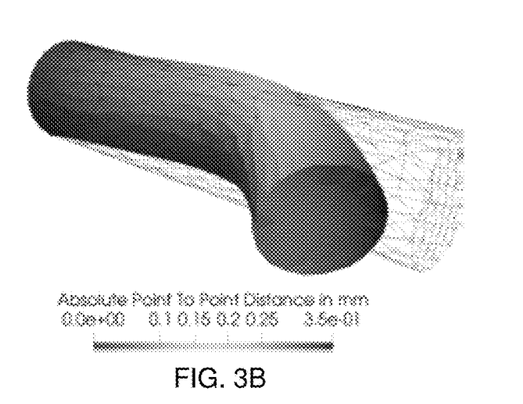
Figure 3C:
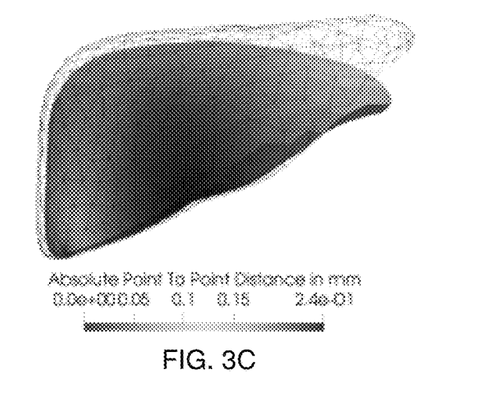
Figure 3D:
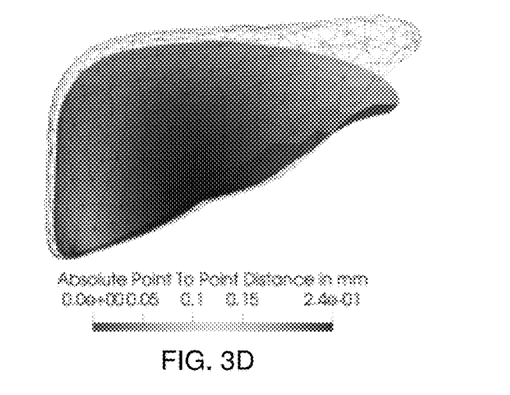

FIGS. 3A-D show examples of AI-based deformation simulation for both the cylinder (FIGS. 3A-B) and the liver (FIGS. 3C-D). The initial state is shown as a wireframe. The mesh is grayscale coded with the absolute point-to-point distance to the TLED ground truth. In FIGS. 3A and 3C, the machine-learned network predicts ten steps ahead and is compared to the TLED simulation. In FIGS. 3B and 3D, the machine-learned network predicts ten steps ahead and is evaluated against TLED using the same time step. The absolute difference between the two simulations is lower than 3.5 mm, which is less than 1% of the overall dimension of the object, highlighting the accuracy of the approach.

The task of the machine-learned network is, given the current state of the continuum, to predict the point-wise accelerations to move for a much larger time step than in explicit finite element analysis. Thus, the computational cost may be reduced for the image processor, and real-time simulations may be enabled. By making point-wise predictions, the machine-trained network may work for arbitrary meshes.

The AI is initialized using the tissue model, even in application. In other embodiments, another machine-learned network is used to initialize based on input of the scan data and/or tissue properties.

A large set of soft tissue deformations are generated given a reference geometry and varying the boundary conditions and forces. These simulations are calculated using a biomechanical solver at a small time step $dt_{train}$ to ensure numerically accurate solutions. The neural network is trained, given the instantaneous acceleration, velocity and displacement with respect to the rest position of a node on the soft tissue 3D mesh, to predict the apparent acceleration to move that node at a timestep $dt_{predict} \gg dt_{train}$. In particular, $dt_{predict}$ may be beyond the Courant-Friedrichs-Lewy limit of the biomechanical solver. As a result, an accurate deformation may be predicted at much higher frame-rate. The neural network is trained to predict nodal apparent accelerations. To make the framework rotation invariant, the training data is augmented through random rotations or the quantities are expressed in a local coordinate system that is rotation invariant.

FIG. 4 shows one embodiment of a system for organ or soft tissue deformation prediction. The system determines the position of the organ at one or more different times. The system implements acts 12-19 of the method of FIG. 1. Other methods or acts may be implemented.

The system includes a medical imaging system 66, a memory 62, an image processor 60, and a display 68. Additional, different, or fewer components may be provided. For example, a network or network connection is provided, such as for networking with a medical imaging network or data archival system. In another example, more than one medical imaging system 66 is provided. In yet other examples, the system is for animation or gaming, so does not include the medical imaging system 66.

The image processor 60, memory 62, and/or display 68 are part of the medical imaging system 66. Alternatively, the image processor 60, memory 62, and/or display 68 are part of an archival and/or image processing system, such as associated with a medical records database workstation or server. In other embodiments, the image processor 60, memory 62, and display 68 are a personal computer, such as desktop or laptop, a workstation, a server, a network, or combinations thereof. The image processor 60, display 68, and memory 62 may be provided without other components for acquiring data by scanning a patient (e.g., without the medical imaging system 66).

The medical imaging system 66 is a medical diagnostic or therapeutic imaging system. Ultrasound, CT, x-ray, fluoroscopy, PET, SPECT, MR, and/or therapeutic (e.g., x-ray) systems may be used. Other medical imaging systems may be used. The medical imaging system 66 may include a transmitter and includes a detector for scanning or receiving scan data representative of the interior of the patient.

One medical imaging system 66 is shown. Different sets of data may be acquired by scanning the patient with this one medical imaging system 66 at different times and/or with different settings. For multi-modality fusion imaging, different medical imaging systems 66 of a same or different type scan the patient at different times.

Due to the differences in time, modality, settings, and/or period of scanning, tissue, anatomy, or objects represented in one set of data may be displaced relative to the representation in another set of data. This deformation is to be determined for generating an image.

The memory 62 is a graphics processing memory, a video random access memory, a random access memory, system memory, cache memory, hard drive, optical media, magnetic media, flash drive, buffer, database, combinations thereof, or other now known or later developed memory device for storing scan or image data. The memory 62 is part of the medical imaging system 66, part of a computer associated with the image processor 60, part of a database, part of another system, a picture archival memory, or a standalone device.

The memory 62 stores the scan or image data. Sets or frames of data from different times, modes, settings, and/or periods of scanning are stored. For example, data from the medical imaging system 66 acquired at different times for a same patient is stored. The data is in a scan format or reconstructed to a volume or three-dimensional grid format.

The memory 62 stores other information. For example, the values of the input feature vector, the values of the output vector, the connections/nodes/weights/convolution kernels of the deep machine-learnt network, calculated forces, acceleration, velocity, position, mesh, volume elements, and/or displacement vectors (e.g., non-rigid deformation transform) are stored. The image processor 60 may use the memory 62 to temporarily store information during performance of the method of FIG. 1.

The memory 62 or other memory is alternatively or additionally a non-transitory computer readable storage medium storing data representing instructions executable by the programmed image processor 60. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 60 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining deformation over time. The image processor 60 is a single device or multiple devices operating in serial, parallel, or separately. The image processor 60 may be a main processor of a computer, such as a laptop or desktop computer, or may be a processor for handling some tasks in a larger system, such as in the medical imaging system 66. The image processor 60 is configured by instructions, firmware, design, hardware, and/or software to perform the acts discussed herein.

The image processor 60 is configured to model physics in an organ of the patient from the scan data. For example, a biomechanical model uses physics to model an organ over time. The general model is fit to the scan data of the patient. The fitting solves for various parameters of the model, allowing the model to simulate the patient-specific organ over time. The organ is simulated using small time increments to represent the organ over 1-3 seconds, but other periods may be used. The time increment is limited for accurate modeling.

The image processor 60 is configured to predict a surface or volume location of the organ using a machine-trained network. A current or known state of the physics model is input, such as inputting instantaneous values of parameters of the model from one or more times, including a time (i.e., given time modeled by the physics model). In one embodiment, the current state is a sum of forces or collection of forces at a location and the location. In response to the input, the machine-trained network outputs a prediction of the surface location at a different time.

The time step used for the prediction by the machine-trained network may be different than the time step used in the physics model for the patient and/or used in the physics model for training the network. The time step for application or prediction may be an order of magnitude or more greater than the time step used in the physics modeling.

The machine-trained network outputs a prediction of deformation, such as a change in or absolute location or kinematic characteristic (e.g., velocity, force, and/or acceleration). In one embodiment, the network outputs a prediction of acceleration of the surface or volume location of the organ. The image processor 60 is configured to perform temporal integration using the acceleration to derive velocity. Another temporal integration from the velocity provides the predicted position of the surface location.

By repeating for different surface or volume locations of the organ, the machine-trained network outputs deformation at the different surface or volume locations. Each surface or volume location is predicted for one or more other times, providing a sequence of changes from the current state to the state at other times of the organ.

The display 68 is a monitor, LCD, projector, plasma display, CRT, printer, or other now known or later developed devise for outputting visual information. The display 68 receives images, graphics, text, quantities, or other information from the image processor 60, memory 62, or medical imaging system 66.

One or more medical images are displayed. The images use the predicted surface location. The deformation is used for reconstruction, registration, multi-modality fusion, directly, or in other ways to generate an image of the organ or patient. The image may assist in diagnosis and/or treatment. For diagnosis, change over time for the spatial locations or anatomy are provided, giving the physician more spatially accurate information. For treatment, the change over time or real-time guidance assists in applying treatment to the correct location in the patient.

The user input 64 is a mouse, trackball, touch pad, keyboard, touch screen, knobs, dials, buttons, sliders, and/or other input devices. The user input 64 operates with a user interface on the display 68 for receiving user input. The image processor 60 is configured to predict the surface location based on input from the user input 64. For example, a change in mesh location, a change in the organ, added force, modeling of surgery, settings for boundary conditions or tissue characteristics, and/or other input is used to change the current state and/or input to the machine-learned network. The prediction is responsive to the input. In other embodiments, no user input is used for determining the deformation.

The user input 64 may be used to make changes. Since the machine-trained network is used, the prediction occurs quickly, providing feedback in imaging within 2 seconds, 1 second, or less. This real-time response allows for interactivity between the user and imaging. Rather than waiting for a model to process over many seconds to respond to each change, real-time interaction is provided.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for soft tissue deformation prediction, the method comprising:
generating a training database by simulating soft tissue deformation with a biomechanics solver for a plurality of samples over time with first temporal increments;
machine training an artificial neural network to predict a deformation characteristic of a nodal position of a soft tissue model as a function of time from locations and instantaneous biomechanical characteristics of the samples over time calculated from the biomechanical solver;
predicting, by the trained artificial neural network, the soft tissue position from a current location and instantaneous biomechanical characteristics from the biomechanical solver, the predicted soft tissue position being with a second temporal increment greater than the first temporal increment; and
generating an image of the soft tissue after deformation.

2. The method of claim 1 wherein simulating and predicting comprise simulating and predicting with the second temporal increments being at least 500 times the first temporal increments.

3. The method of claim 1 wherein machine training comprises performing learning a deep neural network, with an architecture based on feed-forward, and/or recurrent neural networks with long-short-term memory or gated recurrent units.

4. The method of claim 1 wherein machine training and predicting comprise machine training and predicting with the instantaneous forces comprising a sum of external forces, surface forces, and internal forces.

5. The method of claim 1 wherein predicting comprises determining the soft tissue position from a temporal integration of an acceleration.

6. The method of claim 5 wherein determining comprises temporally integrating a velocity from the acceleration and temporally integrating the soft tissue position from the velocity.

7. The method of claim 6 further comprising applying boundary conditions for the acceleration, the velocity, and/or the soft tissue position after predicting.

8. The method of claim 1 wherein generating comprises simulating the soft tissue deformation as a sequence of meshes over time with the first temporal increments, wherein the locations for machine training are locations of nodes of the meshes, and wherein predicting the soft tissue position is predicting a nodal position of a mesh of the soft tissue.

9. The method of claim 1 wherein generating the image comprises reconstructing an image from scan data where the reconstructing uses the predicted soft tissue deformations, generating the image with a registration from different scans of llthell a patient where the registration is based on the soft tissue deformations, or generating an image simulated from a modeled change where the soft tissue position is used to solve a model used to simulate the modeled change.

10. The method of claim 1 wherein predicting comprises predicting in response to a user input of a change to the soft tissue state.

11. A method for soft tissue deformation prediction by a medical imaging system, the method comprising:

scanning, by the medical imaging system, a patient;
estimating a mesh for a soft tissue from scan data from the scanning, the mesh representing the soft tissue at a first time;
fitting a biomechanical model;
predicting, by a machine-learned artificial neural network, a deformation of the mesh at a second time from a mechanical state indicated by the biomechanical model for the first time; and
generating an image of the soft tissue, the image being based on the predicted deformation.

12. The method of claim 11 wherein predicting comprises predicting the deformation as a position of the mesh at the second time.

13. The method of claim 11 wherein the machine-learned artificial neural network was trained using a first time increment and wherein predicting comprises predicting by the machine-learned artificial neural network with a difference between the first and second times being greater than the first time increment.

14. The method of claim 11 wherein predicting comprises predicting with the mechanical state comprising a sum of instantaneous forces.

15. The method of claim 11 wherein predicting comprises predicting an acceleration and determining a nodal location of a mesh from a temporal integration scheme of the acceleration.

16. The method of claim 11 further comprising receiving user input, and wherein predicting comprises predicting based on the user input and within a second of receiving the user input.

17. A system for soft tissue deformation prediction, the system comprising:

at least one medical imaging system configured to acquire scan data representing a patient;

an image processor configured to model physics in of soft tissue of the patient from the scan data, and to predict a location of the soft tissue by application of a current mechanical state from the model of physics to a machine-trained artificial neural network;

a display configured to display an image based on the soft tissue model location.

18. The system of claim 17 wherein the machine-trained artificial neural network was trained with simulations at a first time step, and wherein the image processor is configured to predict the soft tissue model with a second time step larger than the first time step.

19. The system of claim 17 wherein the image processor is configured to model the physics with a biomechanical model, and wherein the application to the machine-trained artificial neural network results in output of an acceleration, the soft tissue model location being from a temporal integration from the predicted acceleration.

20. The system of claim 17 further comprising a user input, wherein the image processor is configured to predict the soft tissue model location in real-time with input from the user input.

* * * * *